United States Patent [19]

Pungor et al.

[11] Patent Number: 5,378,816
[45] Date of Patent: Jan. 3, 1995

[54] METHODS FOR HIGH PURITY CHROMATOGRAPHIC SEPARATION OF PROTEINS HAVING EGF-LIKE BINDING DOMAINS

[75] Inventors: Erno Pungor, Foster City; Les Johnson, West Pittsburg; Monica R. Foermer, San Francisco, all of Calif.

[73] Assignee: Berlex Laboratories, Inc., Cedar Knolls, N.J.

[21] Appl. No.: 991,800

[22] Filed: Dec. 16, 1992

[51] Int. Cl.$^6$ ............................................. A61K 37/00
[52] U.S. Cl. .................................. 530/412; 530/324; 530/399; 530/416
[58] Field of Search ................ 530/399, 412, 416, 324

[56] References Cited

PUBLICATIONS

Parkinson *J Biol Chem* 265, 12602, 1990.
Alpert *J Chromatogr* 185, 375 1979.
Kitagawa *J Chromatogr* 443, 133 1988.

Primary Examiner—Robert J. Hill, Jr.
Assistant Examiner—David Lukton
Attorney, Agent, or Firm—Townsend and Townsend Khourie and Crew

[57] ABSTRACT

Proteins having an epidermal growth factor-like binding region, such as thrombomodulin, may be recovered and purified on a anion exchange resin, such as a polyethyleneimine resin. Conditioned medium containing recombinantly produced protein is applied to the resin under conditions of pH and ionic strength selected to result in specific binding of the protein to the resin. The column is then washed to remove non-bound proteins and bound proteins other than the desired protein to be separated. The desired protein is then eluted from the column and collected in a medium. Further purification, concentration, and other treatment of the protein may be performed by conventional techniques.

7 Claims, 1 Drawing Sheet

METHODS FOR HIGH PURITY CHROMATOGRAPHIC SEPARATION OF PROTEINS HAVING EGF-LIKE BINDING DOMAINS

BACKGROUND OF THE INVENTION

The present invention relates generally to methods for purifying proteins from biological media and, more particularly, to methods for purifying proteins containing EGF-like domains from conditioned medium.

The recombinant production of high value proteins has become widespread. Typically, a prokaryotic or eukaryotic cellular source is transformed with recombinant DNA encoding the protein of interest, and the transformed cells are grown in a suitable culture medium. The proteins may then be recovered from the growing cells, either by harvesting the cells and disrupting them to release the proteins or by collecting conditioned medium into which the recombinant protein has been secreted. In either case, it is necessary to recover and purify the recombinant protein from the cell culture.

Protein purification may be achieved by a variety of processes, such as chromatography including ion-exchange chromatography, size-exclusion chromatography, affinity chromatography, hydrophobic interaction chromatography, reversed-phase liquid chromatography, and the like. Usually, several separation steps will be performed sequentially in order to recover the recombinant protein at the desired level of purity.

In each step of a protein purification process, competing objectives of purity and recovery must be satisfied. Generally, the higher the purity achieved, the lower the recovery. Because of the high value of most recombinant protein products, it is of great interest to identify separation methods and steps which provide for enhanced purity and recovery with particular proteins or groups of proteins. In addition, it is desirable that the separation methods contain relatively few separation steps and that the chromatographic materials used in separation be easily cleaned and reused. Additionally, it is desirable to employ the least costly chromatographic materials available for performing any particular purification method.

Thrombomodulin is a 105 kD cell membrane protein which possesses anticoagulant activity. Recombinant thrombomodulin (particularly soluble thrombomodulin analogs) promises to be therapeutically useful in the treatment of blood clots and other thrombotic circulatory conditions, such as coronary and pulmonary embolism, strokes, myocardial infarction, disseminated intravascular coagulation, deep vein thrombosis, septic shock, and the prevention of reocclusion following thrombolytic therapy.

Heretofore, purification of soluble recombinant thrombomodulin has been achieved by passage of a conditioned medium over a strong anionic column, such as a quaternary aminoethyl (Q-) Sepharose ® column, followed by affinity chromatography using a thrombin column. While acceptable purity can be achieved, the need to employ an affinity column is expensive and provides a possible source of contamination (in the event that the thrombin is lost from the column during the purification procedure).

The use of affinity chromatography is necessitated by the presence of bovine serum albumin (BSA) in conditioned medium which has been supplemented with calf serum. BSA has an isoelectric point very close to that of thrombomodulin, and separation efficiency suffers during the anion exchange step.

It would therefore be desirable to provide improved methods for the separation and purification of thrombomodulin and similar recombinantly produced proteins from conditioned medium. It would be particularly desirable if the methods provided for very high levels of purification while minimizing losses of the valuable recombinant protein. It would be further desirable if the methods were suitable for purifying very large quantities of the proteins, while utilizing relatively inexpensive chromatographic materials and extending the useful life of such materials.

SUMMARY OF THE INVENTION

Improved methods for the separation and purification of thrombomodulin and structurally similar proteins from conditioned medium comprise applying the conditioned medium to an anion exchange resin (as described below) under loading conditions which result in selective binding of the protein to the column. The column is washed to remove non-bound proteins and contaminants, and the protein then eluted. It has been found that highly selective binding occurs between the anion exchange functionalities (as described below) and an EGF-like binding domain present on the thrombomodulin molecule and other related proteins. Useful loading conditions for the weak anionic resins comprise a pH from 4 to 4.5 and an ionic strength from 0 mM NaCl to 400 nM NaCl. Recovery of the proteins from the anion exchange resin may be achieved by increasing the pH of the eluted medium relative to the loading condition. Surprisingly, such methods have been found to provide substantially quantitative recovery of the thrombomodulin or similar protein from conditioned medium with substantially complete separation of BSA which was present in the conditioned medium initially applied to the column.

In a preferred aspect of the present invention, the anion exchange column comprises a resin having anion exchange functionalities attached by a spacer arm which is sufficiently long to permit interaction between the functionalities and the EGF-like binding domain of the protein being separated. Usually, the spacer arm comprises at least about 5 backbone atoms, where the anion exchange functionality will be present at the distal end of the spacer arm and may be present at one or more locations along the length. Preferred anionic functionalities include polyethyleneimine (PEI) and diethylaminomethyl (DEAM).

The thrombomodulin or other protein in the elution medium (i.e., after the anion exchange step but prior to further purification) will typically have a purity of at least about 95% by weight, preferably being at least about 99% by weight. Further purification of the protein, however, can be achieved by various techniques, including chromatography, e.g., using a thrombin column, hydrophobic interaction chromatography, and the like.

The separation methods of the present invention enjoy a number of advantages and result in a very specific (pseudo-affinity) binding and separation of thrombomodulin and certain other proteins containing an EGF-like binding domain, notably being able to substantially completely separate BSA (which has a very close isoelectric point). The methods may be applied to a variety of (but not all) proteins having EGF-like binding domains, requiring only minor modification of the process conditions for a particular protein. The use of anion exchange resins which have the structure described above have also been found to provide very good binding kinetics so that binding may be achieved at relatively high volumetric throughputs. Additionally, the methods of the present invention do not require the use of detergents, solvents, or the like, improving process economics and simplifying eventual process validation with regulatory authorities.

DESCRIPTION OF THE SPECIFIC EMBODIMENT

Figure 1:
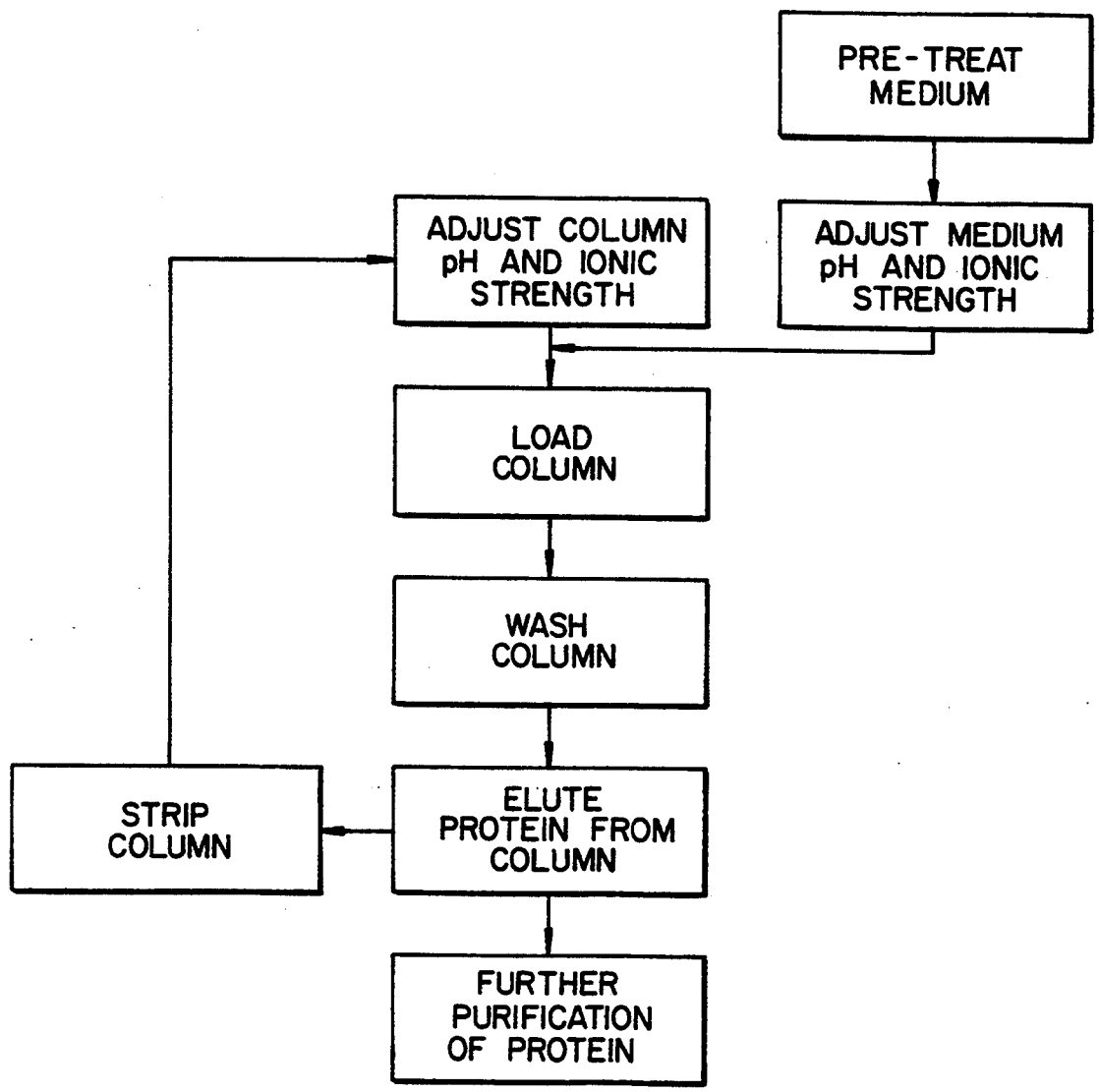
FIG. 1 is a block diagram illustrating the processing steps of the method of the present invention.

The methods of the present invention are suitable for recovering and purifying a variety of proteins from recombinant production media, such as conditioned media, cell lysates, cell pastes, and the like. In particular, the present invention is suitable for recovering and purifying proteins having an epidermal growth factor (EGF)-like binding domain. The method will find its greatest use in separating thrombomodulin, The method has been found not to work on DSPA.

Suitable methods for producing recombinant proteins are well known and described in the scientific literature. Such methods for producing recombinant proteins in prokaryotic and eukaryotic host cells are described, for example, in *Molecular Cloning: A Laboratory Manual*, 2nd ed., Vol. 1-3, ed. Sambrook, et al., cold Spring Harbor Laboratory Press (1989) and *Current Protocols in Molecular Biology*, ed. F. Ausubel et al., Greene Publishing and Wiley-Interscience: New York (1987 and periodic updates), both incorporated herein by reference. Such proteins are usually "heterologous" proteins, i.e., their coding sequences are obtained from an organism other than the host cell in which they are expressed; or the cloned nucleic acid sequence encoding the protein has been altered by deletion, insertion, rearrangement, or replacement; or such proteins are expressed in a different fashion than would be observed in the host cell.

The most commonly used prokaryotic hosts are strains of *Escherichia coli*, although other prokaryotes, such as *Bacillus subtilis* or Pseudomonas may also be used, as is well known in the art.

Preferred eukaryotic host cells include yeast, filamentous fungi, plant, insect, amphibian or avian species. Particularly preferred is the use of mammalian cells. Propagation of mammalian cells in culture is discussed, for example, in *Tissue Culture*, Kruse and Patterson, ed., Academic Press (1973), incorporated herein by reference. Examples of commonly used mammalian host cell lines are Chinese hamster ovary (CHO) cells, VERO cells, HeLa cells, and WI38, BHK, and COS cell lines, although it will be appreciated by the skilled practitioner that other prokaryotic and eukaryotic cells and cell lines may be appropriate for a variety of purposes, e.g., to provide higher expression, desirable glycosylation patterns, or other features.

Examples of workable combinations of cell lines and expression vectors are described in Sambrook et al. (1989) or Ausubel et al. (1987); see also, e.g., Metzger et al., *Nature* 334:31-36 (1988), incorporated herein by reference. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include the promoter regions for metallothionein, 3-phosphoglycerate kinase or other glycolytic enzymes such as enolase or glyceraldehyde-3-phosphate dehydrogenase, enzymes responsible for maltose and galactose utilization, and others. Suitable vectors and promoters for use in yeast expression are further described in Hitzeman et al. EP 73,657A. Appropriate nonnative mammalian promoters include the early and late promoters from SV40 (Fiers et al, (1978) *Nature* 273:113) or promoters derived from Moloney murine leukemia virus, mouse mammary tumor virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences, see, e.g., *Enhancers and Eukaryotic Gene Expression*, Cold Spring Harbor Press, N.Y. (1983), incorporated herein by reference.

Particular expression vectors, cell lines, and methods for the production of recombinant soluble thrombomodulin analogs are described in copending application Ser. Nos. 07/406,941; 07/506,325; and 07/568,456, the full disclosures of which are incorporated herein by reference.

The methods of the present invention rely on use of an anion exchange resin for selectively binding to the EGF-like domain on the protein to be separated. It has been found that the anionic functionality of the resin (spaced-apart from the surface of the resin as described below) is able to bind to the EGF-like domain under preselected resin loading conditions while reducing (although not necessarily entirely eliminating) binding to other proteins and contaminants generally found in the recombinant medium, particularly conditioned culture medium. In particular, it has been found that the anion exchange resins are able to selectively bind to thrombomodulin even in the presence of contaminating proteins having a very similar pI, such as bovine serum albumin (BSA) which has a pI within one pH unit of the pI of thrombomodulin. The ability to select between thrombomodulin and BSA is particularly important to the present invention since the medium used to culture the cells expressing the thrombomodulin will frequently be supplemented with fetal calf serum (FCS) which contains large amounts of BSA. BSA is often the major protein contaminant in the medium and must be completely removed before the protein will be considered purified for pharmaceutical use.

Preferred anion exchange resins will have anionic functionalities which are attached to a matrix by a spacer arm. The resin matrix may take a variety of conventional forms, such as crystalline silica, e.g., diatomite; polymeric beads, such as styrene-divinyl benzene beads; and the like. The resin matrix will be derivatized to covalently bind the spacer arm, and the spacer arm will typically have a backbone of at least five atoms, usually from five to 25 atoms. The anionic functionalities may be located at the remote or distal end of the backbone away from the point of resin attachment, and may also be spaced-apart along the backbone at two or more locations.

Preferred spacer arms include polyethyleneimine (PEI) and diethylaminomethyl (DEAM). PEI spacer arms have the general formula $(CH_2CH_2NH)_x$, where x is from three to 10. Preferred DEAM spacer arms have the formula $(CH_2CH_2NCH_3)_x$, where x is from three to 10.

Referring now to FIG. 1, the method of the present invention comprises applying the biological medium containing the protein to be purified, typically a conditioned medium from the cell culture producing the recombinant protein, to the anion exchange resin under loading conditions which result in selective binding between the resin and an EGF-like domain on the protein. Usually, the biological medium will be pre-treated to remove cellular debris and other particulate contaminants, usually by filtration using a suitable filter, such as a submicron filter. The pH and ionic strength of the conditioned media will be adjusted to values which result in selective binding of the protein to the anion exchange resin, and a physiologically acceptable buffer may also be added. For the recovery and purification of thrombomodulin using a PEI resin, the conditioned medium will be adjusted to a pH in the range from about 4 to 4.5, usually being about 4.5, and an ionic strength in the range from about 0 mM NaCl to 400 mM NaCl, usually being about 400 mM NaCl. Suitable physiologically acceptable buffers include sodium acetate, usually at a concentration about 50 mM.

The anionic resin will also be equilibrated to the same pH as the conditioned medium, e.g., 4.5 for thrombomodulin, usually in the presence of the same buffer. The resin material may be contained in any suitable contact vessel, usually being in a column.

The pretreated conditioned medium is then applied to the equilibrated resin material at a flow rate which permits substantially complete binding of the protein to be recovered and purified. The flow rate chosen will depend on the type of column or other contacter, the binding kinetics between the protein and the particular anion exchange functionality employed, the capacity of the resin, and the like. Acceptable flow rates may be determined empirically by increasing the flow rate until "breakthrough" of the protein is detected in the column effluent. Operational flow rates may then be selected to be some amount lower than the breakthrough value, typically being at least 50% lower.

Methods of the present invention will usually be run in a batch mode, with an amount of conditioned media applied to the resin selected to approach the full binding capacity of the amount of resin utilized. The capacity of the resin is effectively enhanced by the fact that the resin does not bind many of the protein contaminants present in a conditioned medium, particularly does not bind to BSA which is a primary contaminant in conditioned medium which has been supplemented with fetal calf serum. As described above, BSA is a major contaminant which must be removed from pharmaceutical compositions which are derived from cell culture. In the case of thrombomodulin, BSA is particularly difficult to remove since its pI is within one unit of the thrombomodulin's pI, rendering removal by conventional chromatographic ion exchange techniques difficult. The present invention is able to provide for separation of thrombomodulin from BSA using a relatively low cost resin while maintaining a highly effective separation.

After the conditioned medium has been applied to the resin, the resin will be washed to remove non-bound proteins and other contaminants. It will be appreciated that the thrombomodulin or other EGF-containing protein will remain tightly bound to the column so long as the wash conditions are selected to be compatible with binding. In the case of thrombomodulin binding to PEI resins, it has been observed that neither increasing the ionic strength (salt concentration) to 1M NaCl nor decreasing the ionic strength to 0 will result in release of the thrombomodulin from the resin. Initially, the resin will be washed with an aqueous buffer having substantially the same pH and ionic strength as the conditioned medium loaded to the column. In the case of thrombomodulin, the column will be washed with an aqueous solution at pH 4 to 4.5, typically in an acetate buffer.

After the resin has been washed free of non-bound proteins (other than the protein to be separated) and contaminants, the column will be eluted to remove the protein of interest. Elution can be effected by applying an aqueous solution to the resin having an increased pH and ionic strength, where the pH and ionic strength are sufficient to release the binding of the protein to the resin. Elution may be effected by means of a salt gradient or preferably using a step elution. For thrombomodulin, preferred elution conditions comprise a pH in the range from 8 to 8.5, an ionic strength in the range from 100 mM NaCl to 500 mM NaCl. Elution will typically occur in a single peak, and the elution medium containing the protein can be collected for further purification and processing. As mentioned above, the thrombomodulin will be tightly bound to the resin at pH 4–4.5 with 0 to 1M NaCl. At the same time by raising the pH to 8, the thrombomodulin will be released from the resin at lower than 500 mM NaCl concentration. This phenomenon shows that the binding of the thrombomodulin is a multi-modal (pseudo-affinity) binding, and is clearly not ionic interaction since raising the pH should make the binding even stronger if it were ionic.

The protein present in the elution medium will typically have a purity of at least about 95% (by weight), preferably being at least about 99%. Typically, the protein will be further purified by conventional means, such as affinity chromatography, to obtain an essentially pure product being substantially free from contaminants. In the case of thrombomodulin, affinity chromatography can be performed using a thrombin column. It should be appreciated that because of the relatively high purity of the starting material, the useful life of the thrombin column will be significantly extended when compared to the use of the column with an impure starting material.

The purified proteins of the present invention may then be concentrated, typically by filtration, or the like, and may eventually be lyophilized or otherwise incorporated into conventional pharmaceutical preparations. Useful concentration and lyophilization methods are well described in the scientific literature.

Although the foregoing invention has been described in detail for purposes of clarity of understanding, it will be obvious that certain modifications may be practiced within the scope of the appended claims.

What is claimed is:

1. A method for purifying thrombomodulin from conditioned medium in the presence of bovine serum albumin, said method comprising:
  applying the conditioned medium to a polyethyleneimine column under loading conditions of pH and ionic strength selected to bind thrombomodulin but not bind BSA and contaminants, wherein the pH is in the range from about 4 to about 4.5 and the ionic strength is in the range of from 0M NaCl to about 400 mM NaCl;

washing the column to remove non-bound proteins and other contaminants;

eluting the bound thrombomodulin from the column in an elution medium, wherein the elution medium has a pH greater than 4.5;

collecting thrombomodulin in the elution medium; and concentrating the thrombomodulin.

2. A method as in claim 1, wherein the polyethyleneimine column comprises polyethyleneimine functionalities having the formula $(CH_2CH_2NH)_x$, where x is three to 10.

3. A method as in claim 2, wherein washing is performed at a pH from 4 to 4.5 and an ionic strength in the range from 400 mM NaCl to 1000 mM NaCl.

4. A method as in claim 3, wherein eluting is performed at a pH from 8 to 8.5 and an ionic strength in the range from 100 mM NaCl to 500 mM NaCl.

5. A method as in claim 1, wherein the thrombomodulin is concentrated by filtration.

6. A method as in claim 5, further comprising applying the elution medium to a thrombin affinity column prior to filtration.

7. A method as in claim 5, further comprising applying the elution medium to a hydrophobic interaction column prior to filtration.

* * * * *